United States Patent
Takahashi et al.

(10) Patent No.: US 6,582,940 B1
(45) Date of Patent: Jun. 24, 2003

(54) METHOD FOR PRODUCING CALCIUM PANTOTHENATE

(75) Inventors: Norikazu Takahashi, Takaoka (JP); Tomoko Nozaki, Takaoka (JP); Sotohiko Eimori, Tonami (JP); Motoo Shiba, Takaoka (JP)

(73) Assignee: Daiichi Fine Chemical Co., Ltd., Toyoma (JP)

( * ) Notice: Subject to any disclaimer, the term of this patent is extended or adjusted under 35 U.S.C. 154(b) by 0 days.

(21) Appl. No.: 09/857,198

(22) PCT Filed: Dec. 22, 1999

(86) PCT No.: PCT/JP99/07215

§ 371 (c)(1),
(2), (4) Date: Sep. 12, 2001

(87) PCT Pub. No.: WO00/39076

PCT Pub. Date: Jul. 6, 2000

(30) Foreign Application Priority Data

Dec. 25, 1998 (JP) .............................. 10-369582

(51) Int. Cl.[7] .......................... C12P 13/04; C12P 13/06; C12P 7/42; C12P 7/40

(52) U.S. Cl. ........................ 435/106; 435/136; 435/146; 435/116; 435/252.33; 435/320.1

(58) Field of Search ................................. 514/557, 563; 562/400; 435/106, 136, 146, 116, 252.33, 320.1

(56) References Cited

U.S. PATENT DOCUMENTS

| 2,389,097 A | 11/1945 | Warnat |
| 4,020,103 A | 4/1977 | Trocki |

FOREIGN PATENT DOCUMENTS

| EP | 0394022 | 10/1990 |
| EP | 0562958 | 9/1993 |
| GB | 1124619 | 1/1967 |
| JP | 165386 | 9/1944 |
| WO | 96/33283 | 10/1996 |
| WO | 97/10340 | 3/1997 |

OTHER PUBLICATIONS

English Language Translation for JP Appln. No. 40–2330, 1965.
English Language Excerpt of Funabashi et al., Report of Riken the Institute of Physical and Chemical Research, 22,681, 1943.
English Language Abstract of JP 165386. (Sep. 27, 1944).
Inagaki et al., Chem. Pharm. Bull., 24, pp. 3097–3102, 1976.
Levy, H. et al., J. Amer. Chem. Soc., 63, pp. 2846–2847, 1941.

Primary Examiner—Theodore J. Criares
Assistant Examiner—S. Jiang
(74) Attorney, Agent, or Firm—Greenblum & Bernstein, P.L.C.

(57) ABSTRACT

A method for preparing nondeliquescent crystalline calcium pantothenate which comprises the steps of: (1) stirring a supersaturated aqueous solution containing calcium pantothenate in a ratio of 60% (W/W) or more, for example, by using a grinder mill, to obtain a crystal suspension; and (2) drying the suspension. A nondeliquescent crystalline calcium pantothenate which is substantially free from an organic solvent can be efficiently prepared.

10 Claims, 6 Drawing Sheets

METHOD FOR PRODUCING CALCIUM PANTOTHENATE

CROSS-REFERENCE TO RELATED APPLICATIONS

This is a National Stage Application under 35 U.S.C. §371 of PCT/JP99/07215, and claims priority under 35 U.S.C. §119(a)–(d) of JP 10-369582, which are incorporated herein in their entireties.

BACKGROUND OF THE INVENTION

1. Field of the Invention

The present invention relates to a method for preparing nondeliquescent, crystalline calcium pantothenate. In addition, the present invention relates to nondeliquescent, crystalline calcium pantothenate which is substantially free from an organic solvent, and relates to a method for preparing thereof.

2. Description of Background Information

Calcium pantothenate (monocalcium bis[(R)-N-(2,4-dihydroxy-3,3-dimethylbutyryl)-β-alaninate]; hereinafter occasionally abbreviated as "PC") is a medicament listed in the Japanese Pharmacopoeia and widely used for prophylactic and therapeutic treatment of pantothenic acid deficiency as well as therapeutic treatment of contact dermatitis, acute and chronic eczema and the like. This substance is highly dissolvable in water, and when the substance is heated in the state of an aqueous solution, a purity of the substance will be reduced by hydrolysis. Accordingly, a method of spraying an aqueous solution and drying the resulting particles with hot air to produce a product in an amorphous form, or a method of precipitating crystals from a methanol solution, and collecting the precipitates by filtration and then drying with warm air to obtain an amorphous product have been used as methods for a large-scale manufacture of a product with a high purity. However, there is a problem that the amorphous products are hygroscopic and they will receive deiquescence with absorption of moisture at use to give solidified powders.

As crystals of calcium pantothenate, α-type, β-type, and γ-type crystals have been known so far, as well as $4CH_3OH.1H_2O$ solvate and monohydrate as crystals added with a solvent (see, Inagaki et al., Chem. Pharm. Bull., 24, pp.3097–3102, 1976, with respect to identification and details of each of the crystal forms). Among them, the $4CH_3OH.1H_2O$ solvate is hygroscopic and deliquescent. Therefore, it has been desired to develop an industrially applicable method for manufacture of the α-type, β-type, or γ-type crystal, or the monohydrate which are nondeliquescent. However, a method which can stably produce any of these nondeliquescent crystals in large quantities and in a convenient manner has not yet been developed.

As for preparation of calcium pantothenate, methods having been proposed include a method comprising the steps of crystallizing PC from an organic solvent such as methanol and dissolving the resulting crystals in water and concentrating the resulting solution, and then adding methanol and heating the mixture to obtain nondeliquescent needles (m.p. 195–196° C.) (Levy, H. et al., J. Amer. Chem. Soc., 63, pp.2846–2847, 1941); a method for obtaining crystals from a methanol solution which are different from those obtained by the aforementioned method of Levy et al. (m.p. 153.5–154° C.) (Funahashi et al., Report of RIKEN (the Institute of Physical and Chemical Research), 22, 681, 1943); a method comprising the step of adding an appropriate amount of water to a methanol solution to deposit crystals (Japanese Patent Publication No. Sho. 40-2330/1965); a method of depositing an optical active product from a water-containing methanol solution (Japanese Patent Publication No. Sho. 49-27168/1974); a method of collecting PC from a methanol solution (Japanese Patent Unexamined Publication No. Sho. 53-108921/1978); a method of preparing a composition using magnesium lactate and the like (EP394022A1); a method comprising the step of collecting PC from a fermented solution wherein methanol is added to an aqueous solution of PC in a high concentration of about 50 W/V % to adjust a methanol concentration to 90 V/V % (EP822989A1); and a method for preparing PC by using a transformant wherein methanol is added toga PC solution in a high concentration of about 45 to 55 W/W % (EP859848A1).

All of the aforementioned methods involve the use of a mixed solvent of water and an alcoholic solvent such as methanol for crystallization, and are not methods to prepare crystalline PC from a PC solution solely in water. The conventional methods involving the use of methanol for crystallization of PC have a problem of residual methanol, and therefore, it has been desired to develop a method of crystallizing PC from an aqueous solution. However, few attempts have so far been made, since PC is highly dissolvable in water.

DISCLOSURE OF THE INVENTION

An object of the present invention is to provide a method for efficiently preparing nondeliquescent crystalline calcium pantothenate from an aqueous solution of calcium pantothenate which is free from an organic solvent such as methanol, and to provide nondeliquescent crystalline calcium pantothenate which is substantially free from an organic solvent.

The inventors of the present invention made intensive studies to achieve the foregoing objects. As a result, they found that the desired nondeliquescent crystalline calcium pantothenate can be efficiently obtained in an industrial scale by vigorously stirring a supersaturated aqueous solution of calcium pantothenate, which is substantially free from an organic solvent, and drying the resulting viscous crystal suspension. The present invention was achieved on the basis of these findings.

The present invention thus provides a method for preparing nondeliquescent crystalline calcium pantothenate which comprises the steps of: (1) stirring a supersaturated aqueous solution containing calcium pantothenate in a content ratio of 60% (W/W) or more to obtain a suspension of a crystal; and (2) drying the resulting suspension.

According to preferred embodiments of the present invention, provided are the aforementioned method wherein the supersaturated aqueous solution is substantially free from an organic solvent; the aforementioned method wherein a seed crystal of the nondeliquescent crystalline calcium pantothenate is added to the supersaturated aqueous solution in step (1), for example, in a ratio of 0.1% (W/W) or more; the aforementioned method wherein the nondeliquescent crystalline calcium pantothenate is a crystalline substance which comprises α-form crystal, monohydrate, or a mixture thereof; the aforementioned method wherein the supersaturated aqueous solution contains calcium pantothenate in a ratio of from 60% to 74% (W/W); and the aforementioned method wherein the stirring is carried out by using a wet crusher.

From another aspect of the present invention, provided are calcium pantothenate which is obtainable by the aforementioned method; nondeliquescent crystalline calcium pantothenate which is substantially free from an organic solvent; and nondeliquescent crystalline calcium pantothenate which is obtained from a supersaturated aqueous solution of calcium pantothenate which is substantially free from an organic solvent. The present invention also provides calcium pantothenate which contains a crystalline component in an amount sufficient to prevent deliquescence and is substantially free from an organic solvent.

In addition, the present invention provides a supersaturated aqueous solution of calcium pantothenate which contains calcium pantothenate in a ratio of 60% (W/W) or more and is substantially free from an organic solvent. This supersaturated aqueous solution is useful for preparation of the nondeliquescent crystalline calcium pantothenate which is substantially free from an organic solvent. The present invention further provides the aforementioned supersaturated aqueous solution which is used for preparing the nondeliquescent crystalline calcium pantothenate which is substantially free from an organic solvent, and a use of the aforementioned supersaturated aqueous solution for preparing the nondeliquescent crystalline calcium pantothenate which is substantially free from an organic solvent.

DETAILED DESCRIPTION OF THE INVENTION

The calcium pantothenate provided by the method of the present invention is a nondeliquescent and crystalline substance comprising a nondeliquescent crystal of calcium pantothenate, and is characterized by being substantially free from an organic solvent. The calcium pantothenate prepared by the method of the present invention comprises at least one kind of the nondeliquescent crystals of calcium pantothenate. A content of the crystal may be equal to or more than a degree which provides detectable peaks by the powder X-ray diffraction analysis, and the residual part may be an amorphous substance. The term "crystalline" used in the specification is intended to exclude a substances wherein calcium pantothenate is in the state of complete amorphous (i.e., the state in which no peak is substantially detectable by the powder X-ray diffraction analysis), and the term encompasses a substance containing an amorphous part, as well as a substance consisting substantially of complete crystals. Accordingly, the term "crystalline" should not be interpreted to exclude a substance containing an amorphous part. The calcium pantothenate of the present invention, however, should contain a sufficient amount of a crystalline component to prevent deliquescence.

The term "nondeliquescent" used in the specification means that a substance is nonhygroscopic (in general, an amount of absorbed moisture is 5% or less at 40° C. under 82% of relative humidity after 24 hours), or not suffered from deliquescence by moisture absorption. More specifically, the term means that no deliquescence is macroscopically observed in a part or whole surface of a solid calcium pantothenate at 40° C. under 82% of the relative humidity within 24 hours. The calcium pantothenate of the present invention comprising an amount of a crystalline component sufficient to prevent deliquescence is an example of the nondeliquescent and crystalline calcium pantothenate.

According to the present invention, nondeliquescent calcium pantothenate which is substantially free from an organic solvent can be obtained by carrying out crystallization and drying without using an organic solvent. A content of an organic solvent in the calcium pantothenate of the present invention is about 1,000 ppm or less, preferably about 500 ppm or less, more preferably about 100 ppm or less. The content of an organic solvent can be measured by a known analyzing method. Specifically, a measurement can be carried out by using gas chromatography.

The calcium pantothenate prepared by the method of the present invention contains, as a nondeliquescent crystal, α-type crystal, β-type crystal, or γ-type crystal, or the monohydrate or a mixture thereof. Characteristic features and classification of the aforementioned crystals are described in detail in the article by Inagaki et al. (Chem. Pharm. Bull., 24, pp.3097–3102, 1976). In general, each of these crystals is definitely distinguishable by the powder X-ray diffraction and infrared absorption spectrum, and therefore, each of the crystals can be identified. The aforementioned four types of the crystals have been known so far as nondeliquescent crystals; however, there is a possibility that a nondeliquescent crystal other than these four types of the crystals may exist. The crystalline calcium pantothenate prepared by the method of the present invention may contain such novel nondeliquescent crystal. The crystals of calcium pantothenate may sometimes cause a transfer, and a crystalline form may sometimes change during a preparation step such as stirring.

The first step of the method of the present invention comprises vigorous stirring of a supersaturated aqueous solution of calcium pantothenate to obtain a crystal suspension. A method for preparing the supersaturated aqueous solution of calcium pantothenate is not particularly limited. Generally, an aqueous solution containing calcium pantothenate can be concentrated to prepare a concentrated aqueous solution containing calcium pantothenate in a ratio of 50% (W/W) or more, preferably 55% (W/W) or more, more preferably 60% (W/W) or more, and most preferably from 60% to 74% (W/W).

The calcium pantothenate used as a starting material desirably has a purification degree as high as possible. Normally, calcium pantothenate prepared by any method can be used, including those obtained by a synthetic method, a method comprising fermentation, or a method applied by a gene recombination technique. The calcium pantothenate may be purified by recrystallization or a conventional purification means and used for the preparation of the aforementioned supersaturated aqueous solution. The calcium pantothenate used for the preparation of the supersaturated aqueous solution may be any one of amorphous, α-type crystal, β-type crystal, γ-type crystal, monohydrate, or $4CH_3OH.1H_2O$ solvate, and a mixture thereof may also be used. When calcium pantothenate in a crystalline form is used, the crystalline form may be different from that of crystals contained in a desired crystalline calcium pantothenate.

The method for concentration is not particularly limited. Since calcium pantothenate tends to cause decomposition by heating, heating should be performed at a temperature as high as possible that causes no decomposition and completed within a short period of time. For example, the concentration can be carried out under reduced pressure at 80° C. or less, preferably 50° C. or less. The concentration can also be carried out by using steam under reduced pressure at a higher temperature if the heating is applied for a very short period of time. The concentration is preferably carried out under reduced pressure of, for example, 100 mmHg or less, more preferably about 60 mmHg or less. For the concentration under reduced pressure, for example, a centrifugal-flow thin-film vacuum evaporators such as "Evapor" produced by Okawara Mfg. Co., Ltd. and an evaporator can be used.

A concentration of calcium pantothenate in the supersaturated aqueous solution may be 50% (W/W) or more, preferably 55% (W/W) or more, more preferably 60% (W/W) or more, and most preferably from 60% to 74% (W/W). When the concentration becomes around 60%, a ratio of crystallization tends to be improved. When the rate exceeds 74%, the solution may sometimes solidify with the progress of precipitation to deteriorate operative performance for handling. When the concentration is below 50%, the crystallization is hardly achievable and efficiency in the drying step will be lowered, which is an undesirable condition. The supersaturated aqueous solution containing calcium pantothenate should be substantially free from an organic solvent. For example, it is desirable that the solution does not contain an organic solvent (e.g., methanol, ethanol, and isopropanol) in an amount that substantially reduces the solubility of calcium pantothenate. Although a trace amount of methanol will be contained in the supersaturated aqueous solution when $4CH_3OH.1H_2O$ solvate is used for the preparation of the supersaturated aqueous solution, such solution is construed as being substantially free from an organic solvent.

Upon the stirring of the supersaturated aqueous solution, addition of a nondeliquescent seed crystal is preferred because the crystallization rapidly proceeds. The amount of the seed crystal is not particularly limited. Preferably the amount may be 0.1% (W/W) or more, more preferably 1% (W/W) or more. The seed crystal may be crystalline calcium pantothenate partially containing an amorphous. Alternatively, a dried crystal may be used as the seed crystal. Crystals containing moisture a slurry in the form of a mixture of water and crystals may also be used. Normally, crystalline calcium pantothenate can be prepared which contains a crystal of the same crystalline form as that of the seed crystal being added. Accordingly, a type of the seed crystal may be chosen depending on a type of a desired product. However, depending on conditions such as the concentration, a crystalline form of the resulting crystalline calcium pantothenate may sometimes be transferred into a crystalline form different from that of the seed crystal used.

When the concentration of calcium pantothenate in the aqueous solution is higher than 50% (W/W) after the addition of the seed crystal, the process also falls within the scope of the present invention. Although the crystallization of the desired product may sometimes proceed without the addition of the seed crystal when the operation is repeated several times or a continuous operation is carried out, the addition of the seed crystal is preferred for the first operation. It is obvious to those of ordinary skill in the art that the addition of the seed crystal is unnecessary when the operation is repeated several times or a continuous operation is carried out as described above, and accordingly, it should be understood that the preparation process which does not involve the addition of the seed crystal also falls within the scope of the present invention.

The means for stirring is not particularly limited, and any ordinary apparatus for mechanical stirring can be used. It is desired that the supersaturated aqueous solution is stirred as vigorously as possible. The stirring can prevent partial solidification and promote the crystallization. For crystallization of the crystalline calcium pantothenate from the supersaturated aqueous solution, the stirring is not essential. However, the stirring is generally essential because a crystallization rate is very slow and a desired product cannot be efficiently produced in an industrial scale without stirring. The term "stirring" used in the specification should be interpreted as its broadest meaning including common stirring operations, as well as means capable of achieving physical effect similar to the stirring in the crystallization step (e.g., vibrations, ultrasonic stirring and the like).

The supersaturated aqueous solution of calcium pantothenate is generally viscous, and when a supersaturated aqueous solution having a concentration of more than 60% (W/W) is used, a crystal suspension in which the crystal deposits may sometimes be too viscous to be efficiently stirred by an ordinary stirring apparatus. For efficient stirring of the viscous supersaturated aqueous solution or the crystal suspension as mentioned above, it is preferred to use a wet grinder mill or a high-viscosity stirring machine. Examples of the wet grinder mill include those of a type in which a milling medium (e.g., balls or beads) is placed in a mill container and vigorous stirring is made to carry out milling, those achieving milling based on friction force or centrifugal force by rotation of a ring medium or grindstone, those achieving a batch operation or a continuous operation and the like. More specifically, an example includes the wet grinder mill described in EP562958A, and a typical product is commercially available as "MICROS" as a trade name from Nara Machinery Co., Ltd. By using a wet grinder mill, homogeneous stirring can be applied to a viscous slurry, and accordingly, a method involving the use of a wet grinder mill for the stirring is a preferred embodiment of the present invention. As a high-viscosity stirring machine, for example, "a DM type stirring machine for high viscosity" produced by Dalton Corporation, "DYMO-Mill" produced by Shinmaru Enterprises, Inc. and the like can be used.

A temperature for the stirring is desirably as high as possible unless decomposition of calcium pantothenate occurs. Normally, the temperature is desirably from 0 to 60° C., preferably from 20 to 50° C. When the temperature is too low, a crystallization rate may sometimes be lowered. In general, it is desirable to conduct the stirring at 20° C. or higher. Generally, the crystallization completes within about 30 minutes to a few hours to give a grease-like suspension. The first step may be carried out according to a batch treatment, or the crystallization treatment may be continuously carried out with an appropriate staying period of time.

The second step of the present invention comprises a drying of the aforementioned suspension. A means for drying is not particularly limited, and the drying can be performed by using a dryer available in the art under appropriate conditions. It is desirable to carry out the drying at a temperature within a range that can prevent amorphous generation by redissolution. For example, the drying can be made at a temperature of 80° C. or lower, preferably 60° C. or lower, under environmental pressure or reduced pressure. When a spray dryer, an instant vacuum dryer, or a medium flowing dryer is used, the drying can be carried out at a higher temperature. Suitably, the drying can be conducted stepwise, and when the drying is made according to a batch treatment, a tray-system dryer (either an air-flow system or a vacuum system), a lyophilizer and the like can be used. The drying can be efficiently carried out by using a dryer for continuous operation which continuously supplies a material and delivers a dried product, for example, belt type continuous vacuum dryer (e.g., "Belmax" produced by Okawara Mfg. Co., Ltd.). For example, a method of drying with stepwise elevation of temperature by using the belt-system continuous vacuum drying apparatus is suitable for the method of the present invention because the process prevents the remelt of a product. Alternatively, a spray drier, an instant vacuum dryer (e.g., an apparatus produced by Hosokawa Micron Corporation), a media slurry dryer (e.g., an apparatus produced by Nara Machinery Co., Ltd.) and the like can be used.

EXAMPLES

The present invention will be explained more specifically by referring to examples. However, the scope of the present invention is not limited to the following examples.

Example 1

Calcium pantothenate (amorphous) (1.24 kg) was added with water and completely dissolved, and the resulting solution was concentrated by using a rotary evaporator under reduced pressure at about 20 mmHg at the external bath temperature of from 35 to 40° C. to obtain a transparent solution containing 65% (W/W) of supersaturated calcium pantothenate. The resulting solution (1.5 L) was transferred into a container of a wet grinder mill ("MICROS MIC-2", Nara Machinery Co., Ltd), and then 10 g of a slurry containing calcium pantothenate monohydrate (65% (W/W)) was added as seed crystals. The mixture was stirred under constant conditions at the temperature of 25° C. at the stirring rate of 500 r.p.m. The slurry of seed crystals used for the operation was obtained by adding 1 g of PC monohydrate powders to 100 g of 65% supersaturated aqueous solution of PC, stirring the mixture at room temperature for 10 minutes, and then standing the mixture for 5 days.

After stirring was continued for 3 hours, a slurry containing deposited crystals was stored at 20° C. for 2 weeks, and then supplied to a belt type continuous vacuum dryer ("Belmax type BV-101", Okawara Mfg. Co., Ltd.) by using a high-viscosity pump to carry out drying at 40° C. for 24.2 minutes, at 80° C. (radiation) for 37.2 minutes, and at 80° C. for 18.6 minutes under conditions at slurry supplying rate of 0.95 kg/hour under a pressure of 7 mmHg. After the drying, 0.66 kg/hour of a white product was obtained as flakes. The water content of the product was 6.3%, and the methanol content was 8 ppm.

Figure 1:
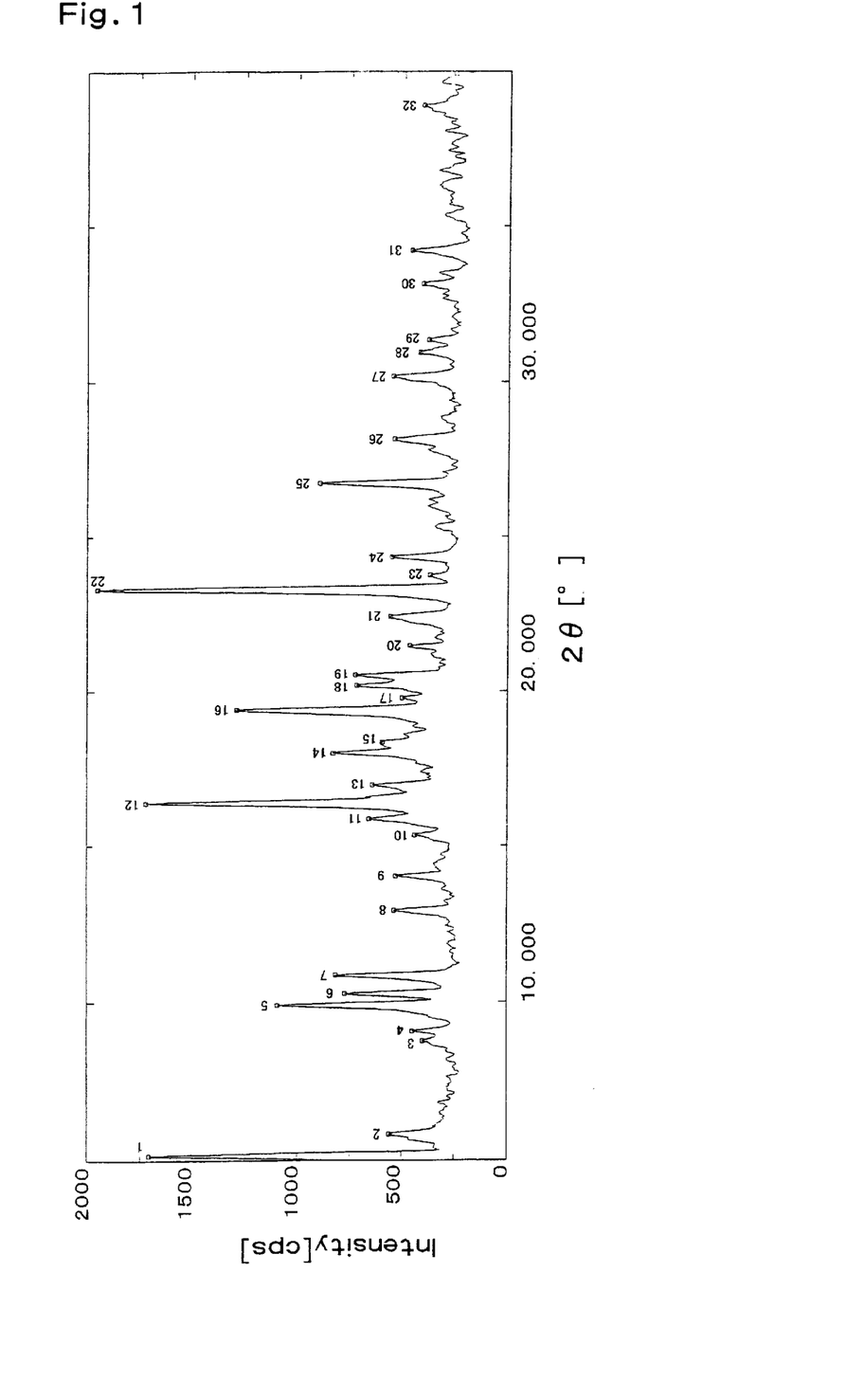
FIG. 1 is the X-ray diffraction pattern of the crystalline calcium pantothenate comprising the monohydrate which was prepared in Example 1.

This product was further dried by using a normal-pressure warm-air dryer at 80° C. for 30 minutes and milled in a mortar, and then sized through a filter No.83 and subjected to a hygroscopicity analysis. The sample (1 g) was placed in a desiccator adjusted to relative humidity of 82% with a saturated aqueous solution of potassium chloride at 40° C., and an amount of absorbed moisture after 24 hours was determined. As a result, the amount of absorbed moisture was found to be 0.7% and no deliquescence was observed. An amorphous was dried in the same manner and the amount of absorbed moisture was determined under the same conditions. As a result, the amount of absorbed moisture was found to be 7.0%, which verified that the calcium pantothenate obtained by the method of the present invention was nondeliquescent. In addition, a weight loss on drying of the aforementioned product was determined by heating to 105° C. for 4 hours according to the method described in the Japanese Pharmacopoeia, and as result, the loss was observed to be 1.8%. Moreover, the powder X-ray diffraction analysis of the aforementioned product gave the characteristic peak indicated by the arrow, which verified that the product was a crystalline substance containing the monohydrate (FIG. 1).

Example 2

Calcium pantothenate (amorphous) (300 g) was added with water and completely dissolved, and the resulting solution was concentrated by using a rotary evaporator under reduced pressure at about 20 mmHg at the external bath temperature of from 35 to 40° C. to obtain a transparent solution containing 67% (W/W) of supersaturated calcium pantothenate. The resulting solution (355 mL) was placed in a separable flask, and then added as seed crystals with 0.5 g of a slurry containing α-form crystals of calcium pantothenate (67% (W/W)) obtained in a similar manner to Example 1. The resulting mixture was stirred under constant conditions at room temperature at a stirring rate of 400 r.p.m. by using a high-viscosity stirring apparatus equipped with three twisted fans and six square fans connected in tandem.

Figure 2:
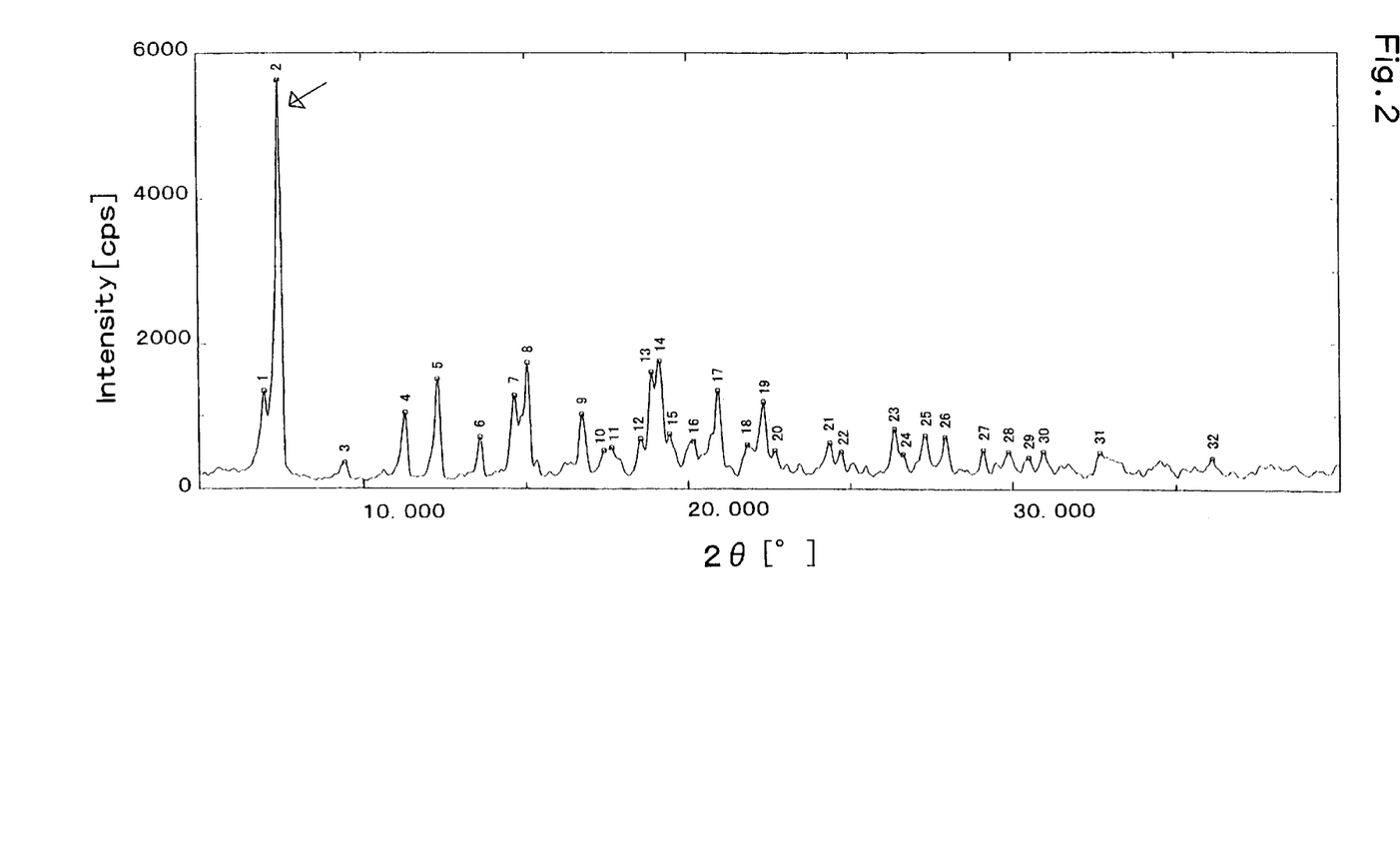
FIG. 2 is the X-ray diffraction pattern of the crystalline calcium pantothenate comprising the α-form crystal which was prepared in Example 2.

After stirring was continued for 2 hours, a slurry containing deposited crystals was spread thinly over a Teflon sheet of a vacuum vat dryer, and the sample of 3 mm thickness was dried under a pressure of 20 mmHg at 55° C. for 5 hours. After the drying, 300 g of a white solid was obtained. The water content of the resulting product was 6.9%. The product was dried with a normal-pressure warm-air dryer at 80° C. for 30 minutes, milled in a mortar, and then sieved through a filter No.140 and subjected to the hygroscopicity analysis according to the method of Example 1. As a result, the amount of absorbed moisture was 0.7% and no deliquescence was observed. The methanol content of this crystalline substance was 20 ppm. The resulting crystalline substance was heated to 105° C. for 4 hours and the weight loss on drying of the aforementioned product was determined. As a result, the loss was found to be 1.7%. Moreover, the powder X-ray diffraction analysis of the aforementioned product gave the characteristic peak indicated by the arrow, which verified that this product was a crystalline substance containing α-form crystals (FIG. 2).

Example 3

A 65% (W/W) aqueous solution of calcium pantothenate was prepared in the same manner as Example 1, and the resulting solution (4.5 L) was transferred into a container of a wet grinder mill ("MICROS MIC-5", Nara Machinery Co., Ltd.). 19.0 g of α-type crystals of calcium pantothenate were added as seed crystals, and then the mixture was stirred under the conditions at a temperature of about 45° C. at the stirring rate of 650 r.p.m. for 1 hour. The seed crystals used in the operation were verified as α-type calcium pantothenate by the powder X-ray diffraction analysis.

Figure 3:
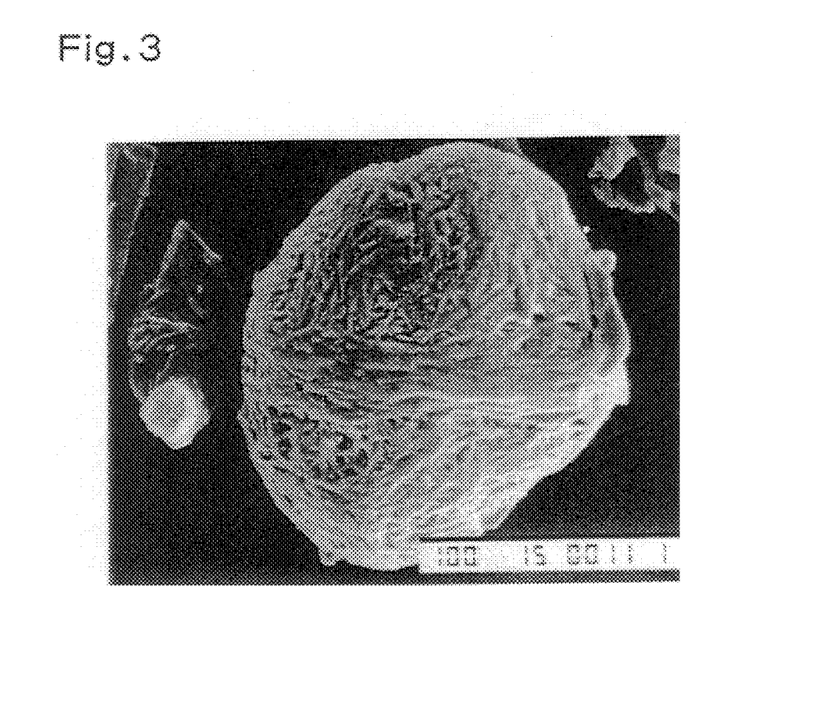
FIG. 3 is the photograph (500 magnifications) under an electron microscope of the crystalline calcium pantothenate comprising the α-form crystal which was prepared in Example 3.

After stirring was completed, the slurry containing deposited crystals was rapidly supplied to a spray dryer ("DA2SW-16", Sakamoto Engineering Co., Ltd.) by using a high-viscosity pump (about 13 kg/hr, for 24 minutes), and then sprayed without further treatment using pressurized air from the two fluid nozzles to carry out spray-drying in a conventional manner. After the drying, 1.36 kg of white powders were recovered from the body of the dryer. The water content of the resulting product was 5.5%. This product was dried by using a normal-pressure warm-air dryer at 80° C. for 30 minutes to obtain crystalline calcium pantothenate. The methanol content of the crystalline pantothenate was 15 ppm. FIG. 3 depicts the photograph (500 magnifications) under an electron microscope showing the state of the crystals.

Figure 4:
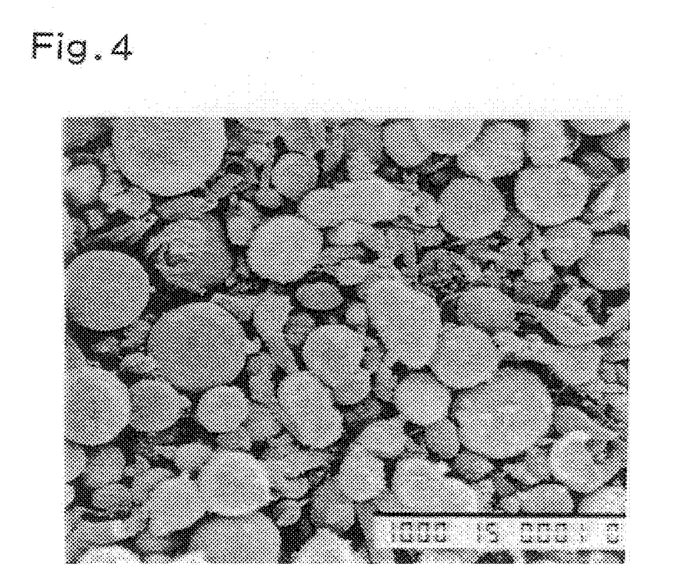
FIG. 4 is the photograph (50 magnifications) under an electron microscope which shows a state of the crystal of the crystalline calcium pantothenate comprising the α-form crystals which was prepared in Example 3 after a hygroscopic test.
Figure 5:
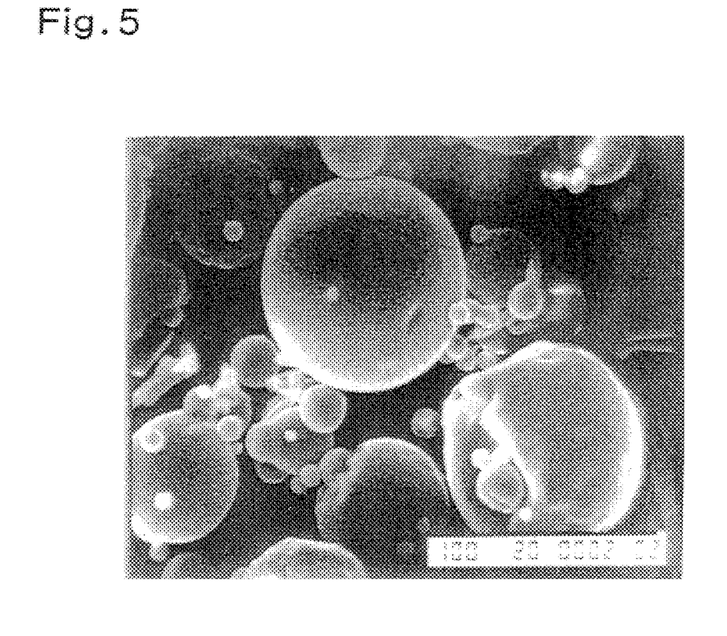
FIG. 5 is the photograph (500 magnifications) under an electron microscope of an amorphous calcium pantothenate.
Figure 6:
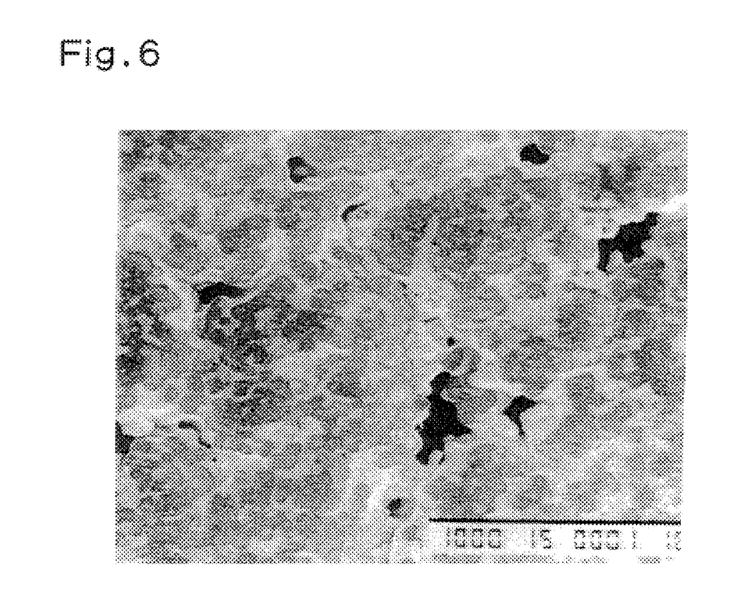
FIG. 6 is the photograph (50 magnifications) under an electron microscope which shows a state of an amorphous calcium pantothenate after a hygroscopic test.

The resulting crystalline calcium pantothenate was subjected to the hygroscopic analysis according to the method in Example 1. As a result, the rate of absorbed moisture was 0.8% and no deliquescence was observed. The photograph (50 magnifications) under an electron microscope revealed almost no change before and after the hygroscopic analysis (FIG. 4). In the photograph of amorphous calcium pantothenate (500 magnifications) under an electron microscope, no wrinkle as evidence of a crystalline substance was observed (FIG. 5). This amorphous calcium pantothenate was subjected to the hygroscopic analysis. As a result, macroscopically apparent deliquescence of the surface was observed during the hygroscopic analysis, and then solidification was observed. After the deliquescence, the state of solidification was observed by the photograph (50 magnifications) under an electric microscope. As a result, no original form as spherical powders was observed and fused state was observed (FIG. 6).

Figure 7:
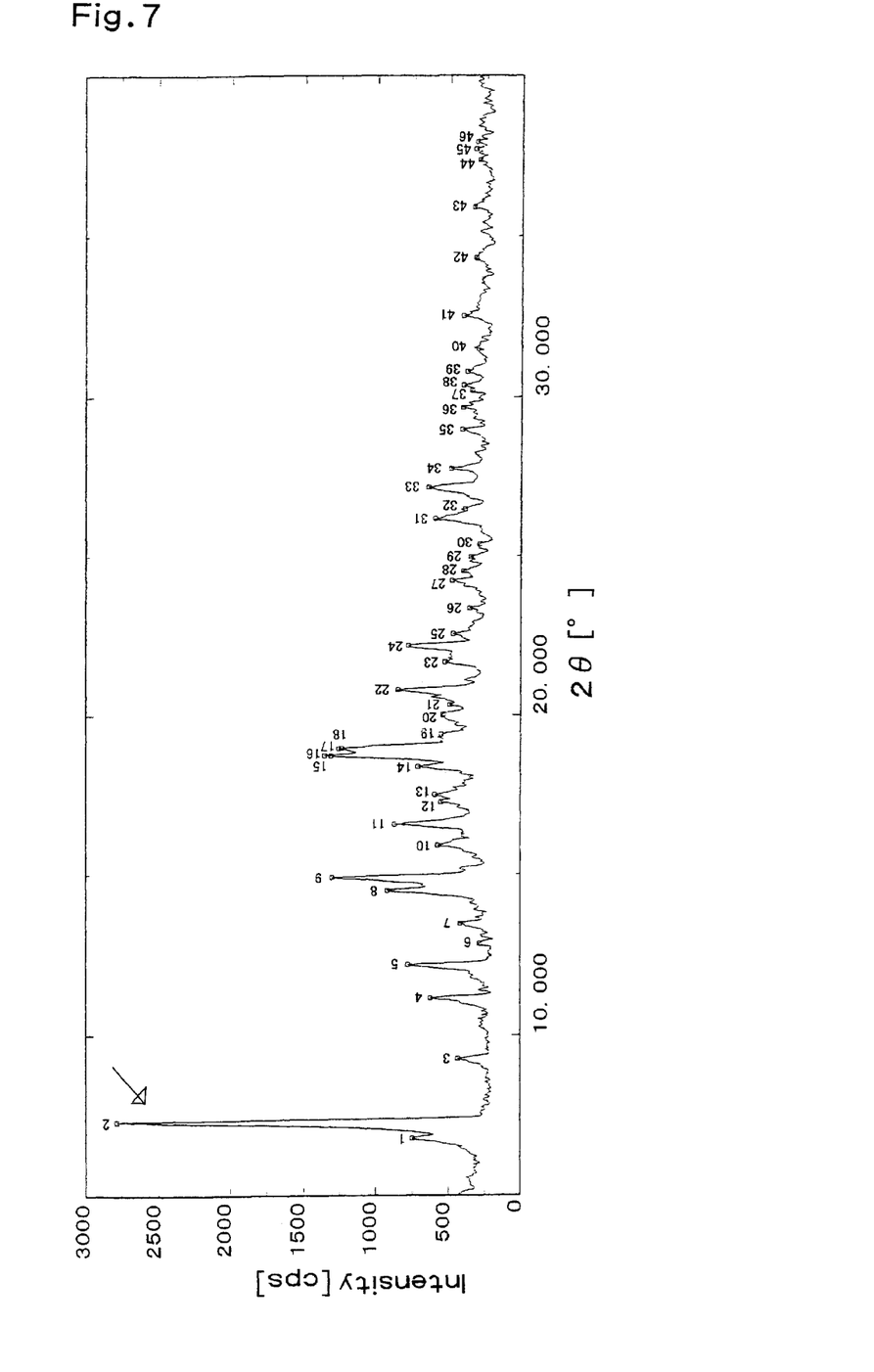
FIG. 7 is the X-ray diffraction pattern of the crystalline calcium pantothenate comprising the α-form crystal which was prepared in Example 3.
Figure 8:
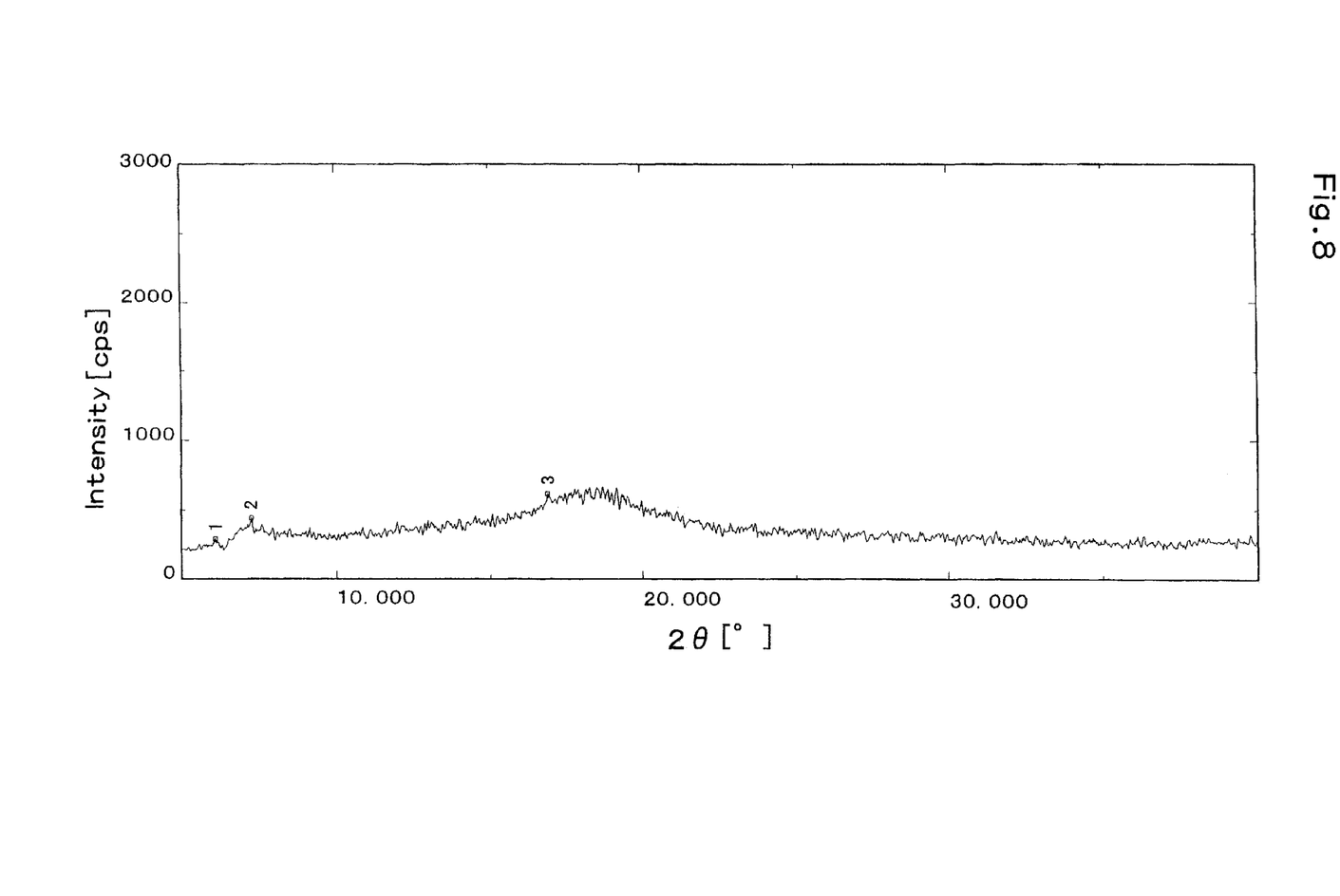
FIG. 8 is the X-ray diffraction pattern of an amorphous calcium pantothenate.

The weight loss on drying of the aforementioned product was measured by heating to 105° C. for 4 hours. As a result, the loss was found to be 2.4%. Moreover, the powder X-ray diffraction analysis of the aforementioned product gave the characteristic peak indicated by the arrow, which verified that this product was a crystalline substance containing α-form crystals (FIG. 7). Whilst no characteristic peak indicating the existence of crystals was observed in the X-ray diffraction pattern of the amorphous calcium pantothenate (FIG. 8).

According to the method of the present invention, crystalline calcium pantothenate which is substantially free from an organic solvent can be efficiently prepared in an industrial scale. The crystalline calcium pantothenate obtained by the method of the present invention is nondeliquescent, and has no solidification or deliquescence. Accordingly, they are easily handled.

What is claimed is:

1. A method for preparing a nondeliquescent crystalline calcium pantothenate comprising:

preparing a supersaturated aqueous solution, without adding an organic solvent, containing calcium pantothenate in a concentration of no less than 60% (W/W);

stirring the solution to obtain a crystal suspension; and drying the suspension.

2. The method of claim 1, wherein the supersaturated solution is substantially free of organic solvent.

3. The method of claim 1, wherein the drying produces a product comprising about 1000 ppm organic solvent or less.

4. The method of claim 1, wherein the drying produces a product comprising about 500 ppm organic solvent or less.

5. The method of claim 1, wherein the drying produces a product comprising about 100 ppm organic solvent or less.

6. The method of claim 1, wherein a seed crystal of a nondeliquescent crystalline calcium pantothenate is added to the supersaturated solution.

7. The method of claim 6, wherein the seed crystal is added in a ratio of 0.1% (W/W) or more with respect to the supersaturated solution.

8. The method of claim 1, wherein the nondeliquescent crystalline calcium pantothenate comprises α-form crystal, monohydrate, or a mixture thereof.

9. The method of claim 1, wherein the supersaturated solution contains the calcium pantothenate in a ratio of from 60% to 74% (W/W).

10. The method of claim 1, wherein the stirring is carried out using a wet grinder mill.

* * * * *

UNITED STATES PATENT AND TRADEMARK OFFICE
CERTIFICATE OF CORRECTION

PATENT NO. : 6,582,940 B1  Page 1 of 1
DATED : June 24, 2003
INVENTOR(S) : N. Takahashi et al.

It is certified that error appears in the above-identified patent and that said Letters Patent is hereby corrected as shown below:

Title page,
Item [73], Assignee, "Toyoma" should be -- Toyama --.

Signed and Sealed this

Third Day of February, 2004

JON W. DUDAS
*Acting Director of the United States Patent and Trademark Office*